United States Patent [19]

Chang et al.

[11] Patent Number: 5,670,173
[45] Date of Patent: Sep. 23, 1997

[54] BIODEGRADABLE POLYMER MEMBRANE CONTAINING HEMOGLOBIN FOR BLOOD SUBSTITUTE

[75] Inventors: Thomas Ming Swi Chang, St-Lambert; Wei-Ping Yu, Montreal, both of Canada

[73] Assignee: McGill University, Montreal, Canada

[21] Appl. No.: 469,782

[22] Filed: Jun. 6, 1995

Related U.S. Application Data

[63] Continuation-in-part of Ser. No. 120,425, Sep. 14, 1993, abandoned.

[30] Foreign Application Priority Data

Sep. 14, 1992 [GB] United Kingdom ............... 9219426
Dec. 24, 1992 [GB] United Kingdom ............... 9226960

[51] Int. Cl.$^6$ .................................................. A61K 35/18
[52] U.S. Cl. .......................... 424/533; 424/529; 424/491; 424/489; 424/450
[58] Field of Search ......................... 424/450, 489, 424/491, 529, 533; 514/2, 21, 10, 8, 832

[56] References Cited

U.S. PATENT DOCUMENTS

| | | | |
|---|---|---|---|
| 4,539,204 | 9/1985 | Ecanow et al. | 514/6 |
| 4,898,734 | 2/1990 | Mathiowitz et al. | 424/426 |
| 4,911,929 | 3/1990 | Farmer et al. | 424/450 |
| 5,100,669 | 3/1992 | Hyon et al. | 424/426 |
| 5,217,648 | 6/1993 | Beissinger et al. | 252/314 |

OTHER PUBLICATIONS

Douglas et al., Crit Rev. Ther Drug Carrier Syst 3 (3) : 233–261 (1987).
Chang, T.M.S., Science, 146, 524 (1964).
Chang, T.M.S., Artificial Cells, Springfield, IL: Charles C. Thomas, 1972.
Chang, T.M.S. et al., Can. J. Physiol. Pharmacol. 44, 115 (1966).
Chang, T.M.S., Geyer, R.P. (editors), Blood Substitutes, Marcel Dekker, New York, (1989).
Chang, T.M.S., Special Symposium Issue on Blood Substitutes, J. Biomaterial Artificial Cells and Immobilization Biotech., 20, 115–1120 (1992).
Djordjevich, L. et al., Exp. Hematol. 8, 584 (1980).
Hunt, A.G. et al., Neomocytes: In Advances in Blood Substitute Research (eds. R.B. Bolin, R. P. Geyer, G. J. Nemo, Alan R. Liss Inc., New York, 59–70 (1983).
Chang, T.M.S. (ed.), Blood Substitutes and Oxygen Carriers, Marcel Dekker, New York, 787 (1992).
Farmer, M.C. et al., J. Biomaterial, Artificial Cells and Organs, 16, 289 (1988).
Tsuchida, E. et al., J. Biomaterial, Artificial Cells and Organs, 16, 313 (1992).
Keipert, P.E. & Chang, T.M.S., Applied Biochem & Biotech., 10, 133 (1984).
Hamilton, P.B. et al., J. Exptl. Med., 85, 477 (1948).
Chang, T.M.S. et al., Can J. Physiol. Pharmacol. 44, 115 (1966).

Primary Examiner—Michael G. Wityshyn
Assistant Examiner—Jean C. Witz
Attorney, Agent, or Firm—Jacobson, Price, Holman & Stern, PLLC

[57] ABSTRACT

The present invention relates to the production of a biocompatible and biodegradable polymer membrane comprising the steps of: a) mixing a polymer selected from the group consisting of polylactic acid, polyglycolic acid and polylactide-co-glycolide with a pharmaceutically acceptable surfactant; b) emulsifying an hemoglobin solution in the mixed solution of step a) to form particles of polymer membrane containing hemoglobin; c) solidifying the particles of step b) by adding cyclohexane; d) separating the solidified particles of step c) by centrifugation; and e) suspending the particles of step d) in a saline solution. In addition another approach uses alcohol-acetone. The biocompatible and biodegradable polymer membrane in accordance with the present invention contains from about 25 to 35% by weight of hemoglobin and has an average diameter from about 0.07 to 1.1μ, preferably a submicron diameter of less than 0.2μ.

7 Claims, 10 Drawing Sheets

| SIZE NANOMETERS | NUMBER: REL. | PERCENT |
|---|---|---|
| 55.6 | 100.0 | 14.9 |
| 65.1 | 97.4 | 14.5 |
| 76.3 | 91.2 | 13.6 |
| 89.5 | 82.3 | 12.3 |
| 105 | 71.4 | 10.6 |
| 123 | 59.6 | 8.9 |
| 144 | 47.9 | 7.1 |
| 169 | 37.1 | 5.5 |
| 198 | 27.6 | 4.1 |
| 232 | 19.8 | 2.9 |
| 272 | 13.6 | 2.0 |
| 319 | 9.0 | 1.3 |
| 374 | 5.8 | 0.9 |
| 438 | 3.5 | 0.5 |
| 513 | 2.1 | 0.3 |
| 601 | 1.2 | 0.2 |
| 705 | 0.7 | 0.10 |
| 826 | 0.3 | 0.05 |
| 969 | | |
| 1135 | | |
| 1331 | | |
| 1560 | | |

FIG_2

| SIZE NANOMETERS | NUMBER: REL. | PERCENT |
|---|---|---|
| 35.3 | | |
| 41.4 | 0.8 | 0.1 |
| 48.5 | 2.4 | 0.4 |
| 56.8 | 6.3 | 1.0 |
| 66.6 | 14.4 | 2.2 |
| 78.1 | 28.4 | 4.3 |
| 91.5 | 48.5 | 7.4 |
| 107 | 71.4 | 10.9 |
| 126 | 90.9 | 13.8 |
| 147 | 100.0 | 15.2 |
| 173 | 95.0 | 14.5 |
| 202 | 78.1 | 11.9 |
| 237 | 55.4 | 8.4 |
| 278 | 34.0 | 5.2 |
| 326 | 18.0 | 2.7 |
| 382 | 8.2 | 1.3 |
| 448 | 3.3 | 0.5 |
| 525 | 1.1 | 0.2 |
| 615 | 0.3 | 0.05 |
| 721 | | |
| 845 | | |
| 991 | | |

FIG_3

| SIZE | NANOMETERS | VOLUME: REL. | PERCENT |
|---|---|---|---|
| 56.8 | | | |
| 66.6 | | | |
| 78.1 | | | |
| 91.5 | | 0.5 | 0.07 |
| 107 | | 1.5 | 0.2 |
| 126 | | 4.3 | 0.7 |
| 147 | | 10.5 | 1.6 |
| 173 | | 22.0 | 3.3 |
| 202 | | 40.0 | 6.0 |
| 237 | | 62.6 | 9.4 |
| 278 | | 84.7 | 12.7 |
| 326 | | 99.0 | 14.9 |
| 382 | | 100.0 | 15.0 |
| 448 | | 87.3 | 13.1 |
| 525 | | 65.8 | 9.9 |
| 615 | | 42.9 | 6.5 |
| 721 | | 24.2 | 3.6 |
| 845 | | 11.8 | 1.8 |
| 991 | | 4.9 | 0.7 |
| 1161 | | 1.8 | 0.3 |
| 1361 | | 0.6 | 0.08 |
| 1595 | | | |
| 1870 | | | |
| 2192 | | | |

FIG. 4

| SIZE | NANOMETERS (LOG SCALE) | REL. VOLUME |
|---|---|---|
| 127 | | |
| 146 | | |
| 169 | | 6.1 |
| 194 | | 11.3 |
| 224 | 1 | 17.5 |
| 258 | | 13.3 |
| 297 | | 8.9 |
| 342 | | |
| 393 | | |
| 453 | | |
| 522 | | |
| 601 | | |
| 692 | | 6.7 |
| 797 | | 49.7 |
| 918 | | 77.4 |
| 1057 | 2 | 100.0 |
| 1218 | | 60.4 |
| 1403 | | 31.3 |
| 1615 | | |
| 1860 | | |

FIG. 5

EFFECT OF pH ON OXYGEN AFFINITY OF POLYMER-HEMOGLOBIN

Circulation Retention of Particles

BIODEGRADABLE POLYMER MEMBRANE CONTAINING HEMOGLOBIN FOR BLOOD SUBSTITUTE

This application is a continuation-in-part of application Ser. No. 08/120,425, filed Sep. 14, 1993, now abandoned.

BACKGROUND OF THE INVENTION a) Field of the Invention

The present invention relates to an oxygen-carrying blood substitute.

b) Description of Prior Art

There is need for an oxygen-carrying blood substitute to be available in emergency situation. The use of donor blood for transfusion is associates with a number of problems such as the availability of blood donors, transmission of hepatitis and AIDS, and short duration of storage. Therefore, there has been a continuing search for red blood cell substitutes.

Hemoglobin solution has been evaluated extensively as an oxygen carrier. The earliest endeavors to use hemoglobin solutions as a blood substitute were limited by such problems as renal damage and rapid removal from circulation (Hamilton, P. B. et al., J. Exptl. Med., 85, 477 (1948)).

In order to overcome these problems, the first artificial red blood cells were created by microencapsulation of hemoglobin solution (Chang, T. M. S., Science, 146, 524 (1964); Chang, T. M. S., Artificial Cells, Springfield, Ill.: Charles C. Thomas, 1972; Chang, T. M. S. et al., Can. J. Physiol. Pharmacol. 44, 115 (1966)).

Collodion, cellulose, HMDA (1,6-hexamethylenediamine), cross-linked protein, bilayer of phospholipid-cholesterol complexed on cross-linked protein membrane and other materials have been used to coat droplets of hemoglobin solution (Chang, T. M. S., Geyer, R. P. (editors), Blood Substitutes, Marcel Dekker, New York, (1989)).

However, these artificial cells with diameters of about one micron survived only for a very short time in the host circulation after intravenous injections. Furthermore, the polymer membrane accumulates in the host body.

Presently, the emphasis is on the use of phospholipids to prepare liposome containing hemoglobin (Chang, T. M. S., Special Symposium Issue on Blood Substitutes, J. Biomaterial Artificial Cells and Immobilization Biotech., 20, 115–1120 (1992); Chang, T. M. S. (ed.), Blood Substitutes and Oxygen Carries, Marcel Dekker, New York, 787 (1992)). The use of submicron phospholipid-cholesterol microcapsules (liposome) has increased the survival time in the circulation (Djordjevich, L. et al., Exp. Hematol. 8, 584 (1980); Hunt, A. G. et al., Neomocytes: In Advances in Blood Substitute Research (eds. R. B. Bolin, R. P Geyer, G. J. Nemo, Alan R. Liss Inc., New York, 59–70 (1983); Farmer, M. C. et al., J. Biomaterial, Artificial Cells and Organs, 16, 289 (1988); Tsuchida, E. et al., J. Biomaterial, Artificial Cells and Organs, 16, 313 (1992)).

The drawbacks of these liposomes are their insufficient stability and strength and also the sensibility of the phospholipid membranes to environmental degradation. Liposomes are subject to degradation during storage and also in the host circulation.

It would be highly desirable to be provided with biocompatible and stable artificial red blood cells, which are made of an artificial polymer for these cells to degrade in the body only after their function have been completed.

It would also be highly desirable to be provided with a biocompatible and biodegradable polymer membrane containing hemoglobin, wherein the enclosed hemoglobin is not denatured.

SUMMARY OF THE INVENTION

One aim of the present invention is to provide a process for the production of biocompatible and stable artificial red blood cells.

Another aim of the present invention is to provide for a process for the production of a biocompatible and biodegradable polymer membrane comprising the steps of: a) mixing a polymer selected from the group consisting of polylactic acid, polyglycolic acid and polylactide-co-glycolide with a pharmaceutically acceptable surfactant; b) emulsifying an hemoglobin solution in the mixed solution of step a) to form particles of polymer membrane containing hemoglobin; c) solidifying said particles of step b) by adding at least one member selected from the group consisting of cyclohexane, ethyl ether and heptane; d) separating said solidified particles of step c) by centrifugation; and e) suspending said particles of step d) in a saline solution.

Another aim of the present invention is to provide for a process for the production of a biocompatible and biodegradable polymer membrane comprising the steps of: a) mixing a polymer selected from the group consisting of isobutyl 2-cyanoacrylate and alkylcyanoacrylate derivatives with phospholipid and tocopherol; b) dissolving the mixed solution of step a) in a solution of ethanol; c) injecting the mixed solution of step b) in an hemoglobin solution to form particles of polymer membrane containing hemoglobin; d) remove ethanol and acetone by dialysis; e) separating said particles of step c) by centrifugation or gel filtration; and f) suspending said particles of step e) in a saline ringer solution.

Another aim of the present invention is to provide for a process for the production of a biocompatible and biodegradable polymer membrane comprising the steps of: a) mixing a polymer selected from the group consisting of polylactic acid, polyglycolic acid and polylactide-co-glycolide with phospholipid and tocopherol; b) dissolving the mixed solution of step a) in ethanol and acetone; c) injecting the mixed solution of step b) in an hemoglobin solution to form particles of polymer membrane containing hemoglobin; d) remove ethanol by dialysis; e) separating said particles of step c) by centrifugation or gel filtration; and f) suspending said particles of step e) in a saline ringer solution.

Another aim of the present invention is to provide for a biocompatible and biodegradable polymer membrane used as an oxygen-carrying blood substitute, comprising a polymer selected from the group consisting of polylactic acid, polyglycolic acid and polylactide-co-glycolide containing from about 25 to 35% by weight of hemoglobin and having an average diameter from about 0.07 to 1.1µ, preferably a submicron diameter of less than 0.2µ.

Another aim of the present invention is to provide for a biocompatible and biodegradable polymer membrane used as an oxygen-carrying blood substitute, comprising a polymer selected from the group consisting of isobutyl 2-cyanoacrylate and alkylcyanoacrylate derivatives containing from about 25 to 35% by weight of hemoglobin and having an average diameter from about 0.07 to 1.1µ, preferably a submicron diameter of less than 0.2µ.

BRIEF DESCRIPTION OF THE DRAWINGS

FIG. 2 is a graph of the Nicomp size distribution analysis of polymer membrane particles consisting of polylactic acid and containing 27% by weight of hemoglobin with a mean diameter of 0.07μ;

FIG. 3 is a graph of the Nicomp size distribution analysis of polymer membrane particles consisting of polylactic acid and containing 28% by weight of hemoglobin with a mean diameter of 0.164μ;

FIG. 4 is a graph of the Nicomp size distribution analysis of polymer membrane particles consisting of polylactic acid and containing 28% by weight of hemoglobin with a mean diameter of 0.389μ;

FIG. 5 is a graph of the Nicomp size distribution analysis of polymer membrane particles consisting of polylactic acid and containing 27% by weight of hemoglobin with a mean diameter of 0.231μ;

FIG. 12 is a curve of the circulation retention of polymer membrane particles consisting of polylactic acid and containing hemoglobin with respect to time.

DETAILED DESCRIPTION OF THE INVENTION

Figure 1:
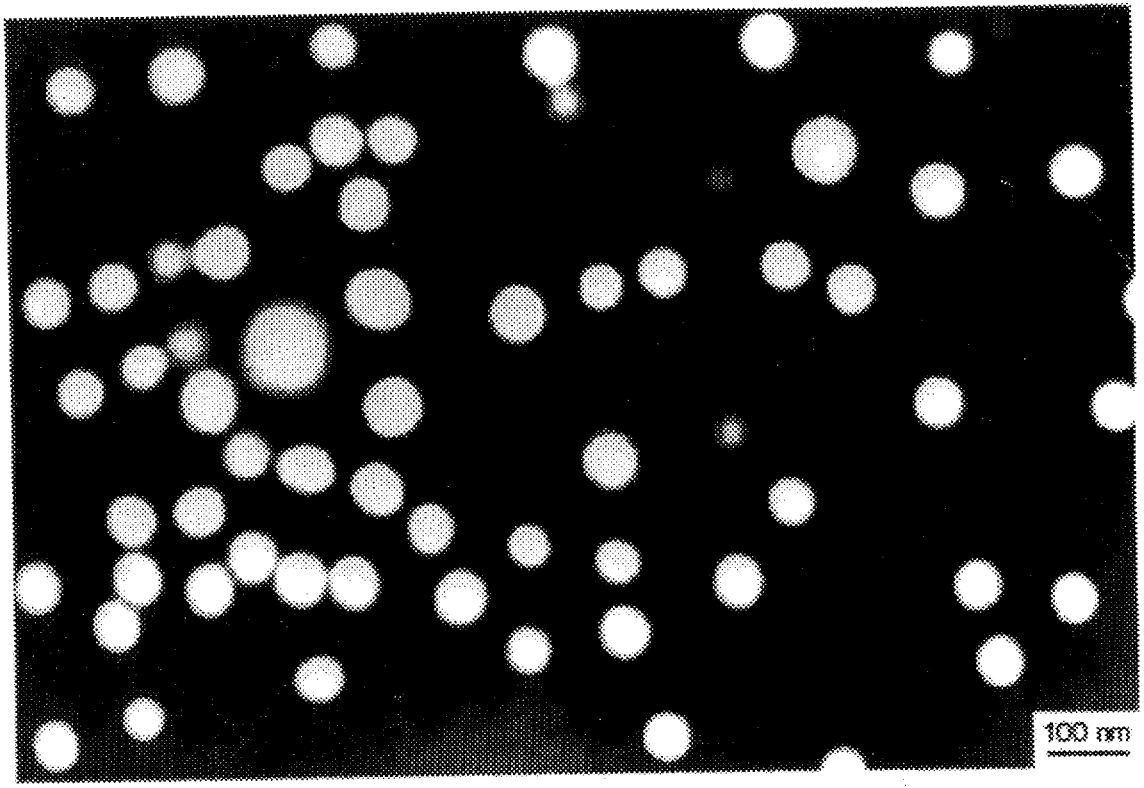
FIG. 1 is a micrograph of polymer membrane particles consisting of polylactic acid and containing 25% by weight of hemoglobin in accordance with the present invention.

In accordance with the present invention, a hypothesis on the formation of biodegradable polymer membrane containing hemoglobin is put forward on interfacial polymer deposition. In the process of preparation, hemoglobin solution is emulsified in a polymer solution. When a non-solvent is added, the polymer is precipitated and deposited at the interface between organic solvents and droplets of the hemoglobin solution. Thus, the membranes were formed.

Because of the instability of hemoglobin, the solvents one can use are limited. Here, chloroform and ethyl acetate are used for polymer solvents, and ethyl ether, cyclohexane and heptane can be used as non-solvents.

In this approach, when L-α-Phosphatidylcholine is used, smaller molecules especially co-factor like 2,3-DPG and pyridoxal phosphate can be retained in biodegradable polymer membrane with human hemoglobin to increase P50. This is not required for bovine hemoglobin.

In another approach alcohol and acetone are used to dissolve the polymer. When added to hemoglobin solution, alcohol and acetone diffuse into the hemoglobin solution and polymer is precipitated to form a polymer membrane particle.

1. Materials:

Polylactic acid (PLA) is obtained from Polysciences Inc. (Canada). Isobutyl 2-cyanoacrylate (IBCA), surfactants (Tween 20™, Span 85™, Triton X 100™, and Pluronic F68™), ethyl cellulose and L-α-Phosphatidylcholine (hydrogenated) and other phospholipids, such as distearoyl phosphatidylcholine (DSPC) or DSPG and tocopherol acetate were obtained from Sigma Chemical Co. (U.S.A.). Dialysis membrane (Spectrapor 5™) is purchased from Fisher Scientific Co.. Diethyl ether, ethyl acetate, cyclohexane, and chloroform are purchased from BDH Chemical (Canada). All the other chemicals are of reagent grade.

2. Preparation of Hemoglobin Solution

Stroma free hemoglobin is prepared according to the method of Keipert & Chang (Applied Biochem. & Biotech., 10, 133, (1984)). Briefly, hemoglobin is obtained by hypotonic hemolysis of bovine red cells and it is made stroma-free by toluene extraction and is clarified by high speed centrifugation.

The resulting solution contained 10 to 15 g hemoglobin/dl. In order to minimize the formation of methemoglobin, the manipulation is carried out at 4° C. and the hemoglobin solution is controlled at pH 7.4.

In accordance with the present invention, other materials usually present inside red blood cells, enzymes such as catalase, superoxide dismutase and methemoglobin reductase, and cofactors amongst others, may be encapsulated in addition to hemoglobin.

3. Preparation of Biodegradable Polymer Membrane Containing Hemoglobin (1) Preparation with Polylactic Acid (dl-PLA)

100 to 150 mg of dl-PLA, 50 to 100 mg phospholipid and 5 mg of tocopherol are dissolved in a mixed solution of ethanol (2 to 5 ml) and acetone (5 to 10 ml). Then this solution is slowly injected into 10 to 30 ml of 0.5 to 10% hemoglobin solution containing 0.1 to 1.0% Tween 20™ under constant magnetic stirring. Diffusion of ethanol and acetone into the aqueous phase resulted in polymer membrane particles formation. The ethanol and acetone in the aqueous phase can be easily eliminated by dialysis against saline solution or phosphate buffer at 4° C. The polymer membrane particles containing hemoglobin can be separated by high speed centrifugation (30,000 g).

(2) Preparation with Isobutyl Cyanoacrylate (IBCA)

50 to 100 mg IBCA, 35 to 50 mg phospholipid and 5 mg of tocopherol are dissolved in 5 to 10 ml of ethanol. Then, this solution is slowly injected into 10 to 25 ml of 0.5 to 10% hemoglobin solution containing 0.1 to 0.5% Tween 20™ under constant magnetic stirring. The polymer membrane particles containing hemoglobin (PMCHb) are simultaneously formed. The ethanol is eliminated by dialysis against phosphate buffer (pH 7.4) at 4° C. The polymer membrane particles containing hemoglobin (PMCHb) may be separated either by high speed centrifugation.

(3) Preparation with Polylactic Acid (1-PLA)

150 mg of 1-PLA, 50 mg of phosphatidylcholine are dissolved in 10 ml of chloroform containing mixed surfactants. 0.5 ml of stroma free hemoglobin solution is emulsified in the solution. 25 ml of diethyl ether is injected into the emulsion under magnetic stirring. The biodegradable polymer membrane containing hemoglobin is simultaneously formed by interfacial polymer deposition.

The particles are solidified by adding cyclohexane. The solidified particles are then separated by centrifugation and are suspended in saline containing surfactant. The mixed suspensions are dialyzed against phosphate buffer (pH 7.4) at 4° C.

(4) Preparation with Polylactic Acid (dl-PLA) and Ethyl Cellulose 100 mg of dl-PLA, 50 mg of ethyl cellulose and 50 mg of phosphatidylcholine are dissolved in 10 ml of ethyl acetate containing mixed surfactants. 0.5 ml of hemoglobin solution is emulsified as for the above solution. Then 25 ml of cyclohexane is injected into ethyl acetate-hemoglobin emulsion under magnetic stirring. The biodegradable polymer membrane containing hemoglobin is simultaneously formed by interfacial polymer deposition. The biodegradable polymer membrane containing hemoglobin formed are solidified by adding another 100 ml of cyclohexane. The solidified polymer membrane particles are then separated by centrifugation and are suspended in saline containing surfactant. The suspensions are dialyzed in saline containing surfactant. The suspensions are dialyzed against phosphate buffer (pH 7.4) at 4° C.

(5) Preparation with Polylatide-co-glycolide 100 mg of PLA, 10 to 50 mg phospholipid and 5 mg of tocopherol are dissolved in 5 to 10 ml of acetone with the help of water bath sonification. This solution is slowly injected into 10 to 30 ml of 0.5 to 10% hemoglobin solution containing 0.1 to 1.0% Tween 20™ under magnetic stirring. The polymer membrane particles containing hemoglobin are formed after the diffusion of acetone into the aqueous phase. The acetone can be removed by dialysis against saline solution or phosphate buffer. The particles can be separated by high speed centrifugation.

Biodegradable Polymers

Besides polyactic acid (PLGA) and polyisobutylcyanoacrylate, other biodegradable polymers may be used in accordance with the present invention, such as PHB, PLA, etc.

Phospholipids

Different phospholipids may be used in accordance with the present invention, for example, hydrogenated egg lecithin (HEPC), hydrogenated soybean lecithin (HSPC) soybean lecithin (SPC), distearoyl phosphatidylcholine (DSPC), and dimyristoyl phosphatidyl glycerol (DMPG). When HSPC or DSPC are added in the preparation, the longer survival time is obtained.

4. Particles Size Determination

The diameter and size distribution of the biodegradable polymer particles containing hemoglobin are determined by using the Nicomp Size Analyzer™ (Model 370). With different polymer and different phospholipid used, the average particle size of the polymer membrane particles of the present invention may vary from 80 to 1100 nm.

The preferred diameter of the polymer membrane particles comprising a polymer selected from the group consisting of polylactic acid, polyglycolic acid and polylactide-co-glycolide in accordance with the present invention is less than 1μ, preferably a submicron diameter of less than 0.2μ.

The preferred diameter of the polymer membrane particles comprising a polymer selected from the group consisting of isobutyl 2-cyanoacrylate and alkylcyanoacrylate derivatives in accordance with the present invention is 165 nm.

5. Hemoglobin Concentration Determination

The biodegradable polymer particles hemoglobin contents in the final production can be adjusted by resuspension of the particles in the different volume of the saline solution. With different formulation, the hemoglobin contents in the particles may vary from 20 to 45%.

Hemoglobin concentration is determined by spectrophotometric analysis using the Sigma's "Total Hemoglobin Kit™". The hemoglobin concentration in the biodegradable polymer membrane is calculated by dosing non-encapsulated hemoglobin.

6. Steady Shear Viscosity Determination

Steady shear viscosity of the suspension of the biodegradable polymer particles is measured with a Wells-Brookfield Syncro-Lectric Microviscometer™ (Model LVT) equipped with a 0.80° cone (model CP-40™). Shear rates are from 45 to 450 $s^{-1}$ at 22 ° C.

7. Oxygen Dissociation of Biodegradable Polymer Particles Containing Hemoglobin

Oxygen affinity of biodegradable polymer particles containing hemoglobin is determined by the TCS Hemoxanalyser (TCS Medical Products Co., U.S.A.,) at 37° C.

8. Ratio of Encapsulation of Hemoglobin

I) Polymer membrane particles consisting of a polymer selected from polylactic acid, polyglycolic acid, and polylactide-co-glycolide.

The hemoglobin encapsulation efficiencies ranged from 29% to 47% of the starting quantities of hemoglobin, depending on the polymer used. Higher amount of hemoglobin is encapsulated with poly(dl)lactic acid. The possible reason is that polymer membrane prepared with poly(dl) lactic acid contained less defects in the membrane than that prepared by poly(l)lactic acid, and so, there is less leakage.

The preferred content of hemoglobin in the polymer membrane particles in accordance with the present invention is more than 25% by weight.

II) Polymer membrane particles consisting of a polymer selected from isobutyl 2-cyanoacrylate and alkylcyanoacrylate derivatives.

The hemoglobin encapsulation efficiencies is 13% of the starting quantities of hemoglobin. The ratio of hemoglobin/lipid/polymer is hemoglobin/DSPC/PIBCA=1/1.1/1.6.

The present invention will be more readily understood by referring to the following examples which are given to illustrate the invention rather than to limit its scope.

EXAMPLE I

Polymer Membrane Particle Consisting of Polylactic Acid (dl-PLA)

The polymer membrane particles are produced using polylactic acid (dl-PLA) and hemoglobin and according to the following procedure.

100 to 150 mg of dl-PLA, 50 to 100 mg phospholipid and 5 mg of tocopherol are dissolved in a mixed solution of ethanol (2 to 5 ml) and acetone (5 to 10 ml). Then this solution is slowly injected into 10 to 30 ml of 0.5 to 10% hemoglobin solution containing 0.1 to 1.0% Tween 20™ under constant magnetic stirring. Diffusion of ethanol and acetone into the aqueous phase resulted in polymer membrane particles formation. The ethanol and acetone in the aqueous phase can be easily eliminated by dialysis against saline solution or phosphate buffer at 4° C. The polymer membrane particles containing hemoglobin can be separated by high speed centrifugation (30,000 g).

The polymer membrane particles are containing 1.5% gm of hemoglobin.

A typical electron micrograph for this preparation of this biodegradable polymer membrane particles containing hemoglobin is shown in FIG. 1. They are spherical and homogeneous. The size of the polymer membrane particles from the micrograph is about 80 to 120 nm. The thickness of the particle membrane is about 5 to 15 nm.

1. Physical properties

The characteristic of these polymer membrane particles containing 1.5% gm of hemoglobin are listed in Table 1 below.

TABLE 1

| Characteristics of polymer-hemoglobin | |
|---|---|
| Hemoglobin concentration | 1.5 gm/dl |
| Polymer concentration | 0.9 gm/dl |
| Phospholipid concentration | 0.4 gm/dl |
| Specific Gravity (22° C.) | 1.0043 |
| Viscosity (37° C.) | 3.2–3.4 cp |
| Hill's coefficient | 2.4–2.9 |
| Bohr coefficient | −0.22—0.24 |

2. Steady Shear Viscosity

The steady shear viscosity of these polymer membrane particles containing 1.5% gm of hemoglobin and rat whole blood at different shear rate (1/sec) are shown in Table 2 below. At 22° C., the steady shear viscosity of the polymer particle preparation is higher than that of rat whole blood. The viscosity of the polymer particle preparation seems to be lowere than that of human blood.

TABLE 2

| Viscosity of the preparation (22° C. cp) | | |
|---|---|---|
| shear rate (1/sec) | vs. prep. | vs. rat blood |
| 45 | 6.5 | 5 |
| 90 | 6.5 | 3.5 |
| 225 | 5 | 3 |

3. Ratio of Encapsulation

The hemoglobin encapsulation efficiency is 10 to 17% of the strating quantities of hemoglobin. The ratio of hemoglobin:polymer:phospholipid is 1:(0.4–1.5):(0.2–1.5).

EXAMPLE II

Particles Size Determination

The diameter and size distribution of the biodegradable polymer membrane of the present invention containing hemoglobin are dependant on the procedure used for their preparation.

The diameter and size distribution are determined by using the Nicomp Size Analyzer™ (Model 370). The instrument operates by light scattering.

The particle size of four preparations determined by Nicomp Size Analyzer™ are presented in FIGS. 2, 3, 4, 5, 7 and 8. A unimodal distribution is obtained for all samples (except FIG. 5). With different emulsification process, and different polymers, the average size of biodegradable polymer membrane containing hemoglobin is varied from 0.074 to 1.1 um.

In this approach, in the case of phase separations using organic solvent the process of emulsification is most important fact which influence the size of the preparation. The best result is obtained by firstly preparing a microemulsion of hemoglobin in polymer solution, then precipitating the polymers. This is achieved by using a mixed surfactants (Tween 20™, 0.4%; Span 85™, 0.5%; phospholipid 0.5 to 1%) combining with mechanic emulsification or sonification. In this case, the biodegradable polymer membrane containing hemoglobin with 74 nm in diameter are prepared.

In the case where alcohol-acetone were used the particle size depends on the concentrations and type of polymer and lipids used.

EXAMPLE III

Determination of Oxygen Affinity of Biodegradable Polymer Membrane Containing Hemoglobin (IBCA)

The polymer membrane particles are produced using isobutyl 2-cyanoacrylate (IBCA) and hemoglobin and according to the following procedure.

50 to 100 mg IBCA, 35 to 50 mg phospholipid and 5 mg of tocopherol are dissolved in 5 to 10 ml of ethanol. Then, this solution is slowly injected into 10 to 25 ml of 0.5 to 10% hemoglobin solution containing 0.1 to 0.5 % Tween 20™ under constant magnetic stirring. The polymer membrane particles containing hemoglobin (PMCHb) are simultaneously formed. The ethanol is eliminated by dialysis against phosphate buffer (pH 7.4 ) at 4° C. The polymer membrane particles containing hemoglobin (PMCHb) may be separated either by high speed centrifugation.

The oxygen absorption curve is determined by the TCS Hemoxanalyser™ ( TCS Medical Products Co., U.S.A.)

Figure 6:
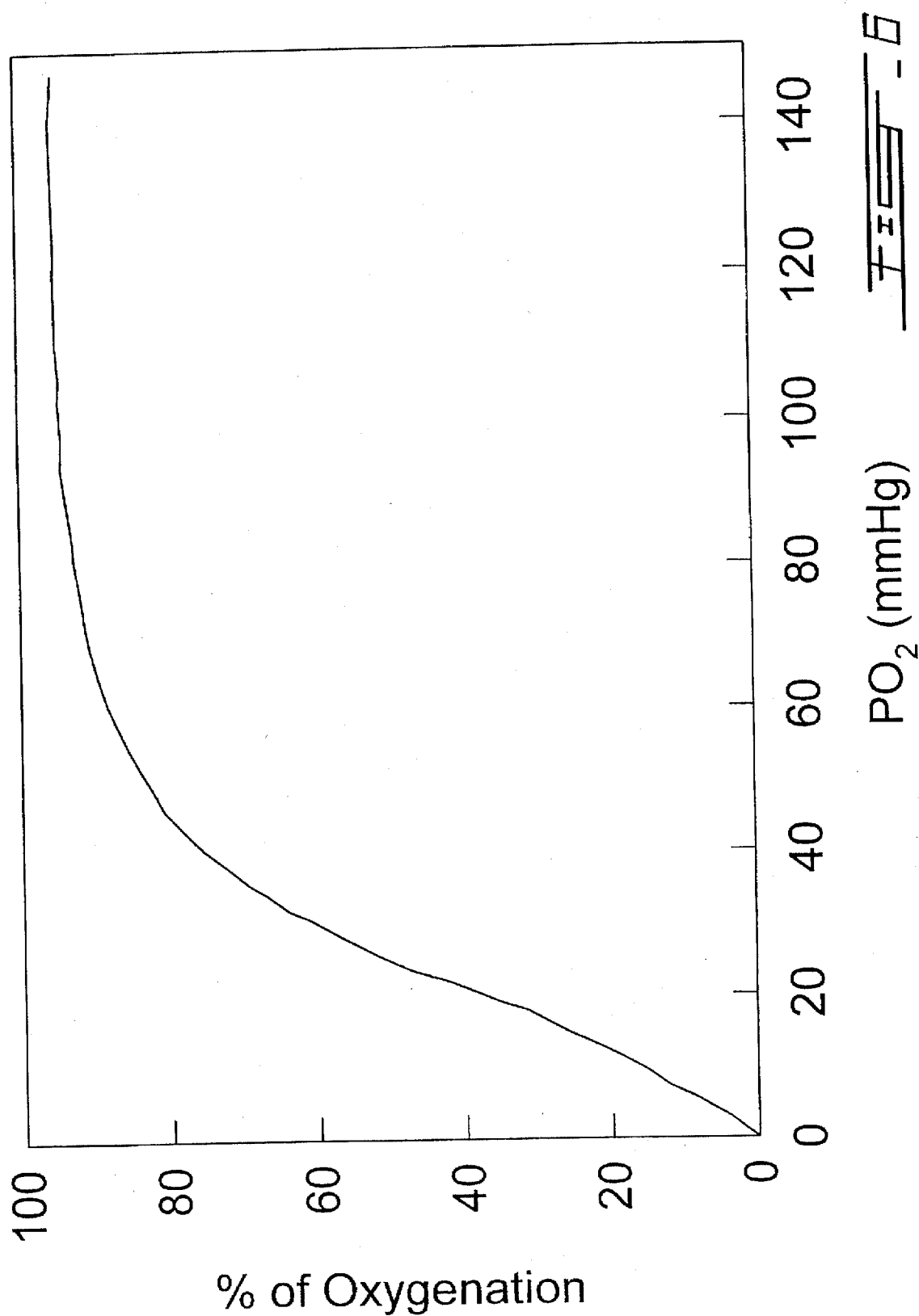
FIG. 6 is an oxygen dissociation curve of polymer membrane particles consisting of polylactic acid and containing 27% by weight of hemoglobin.
Figure 7:
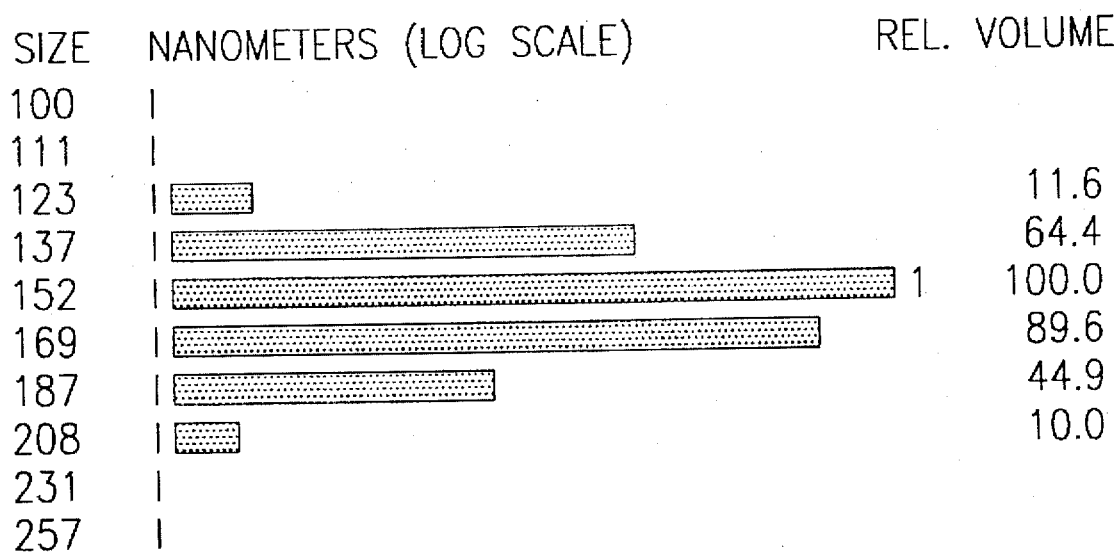
FIG. 7 is a graph of the Nicomp size distribution analysis of polymer membrane particles consisting of isobulty2-cyanoacrylate and containing 27% by weight of hemoglobin with a mean diameter of 0.389μ.
Figure 8:
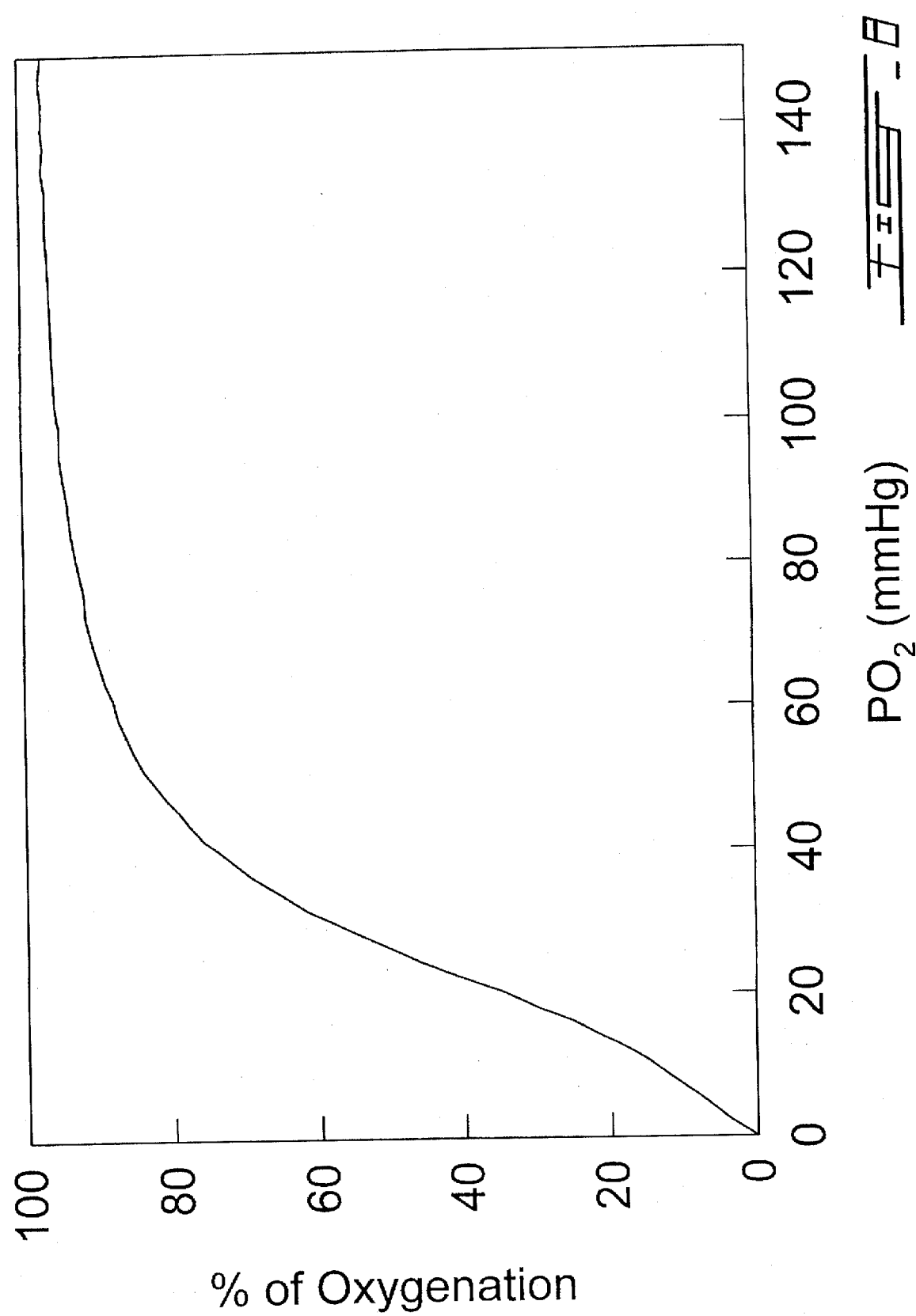
FIG. 8 is an oxygen dissociation curve of an hemoglobin solution.
Figure 9:
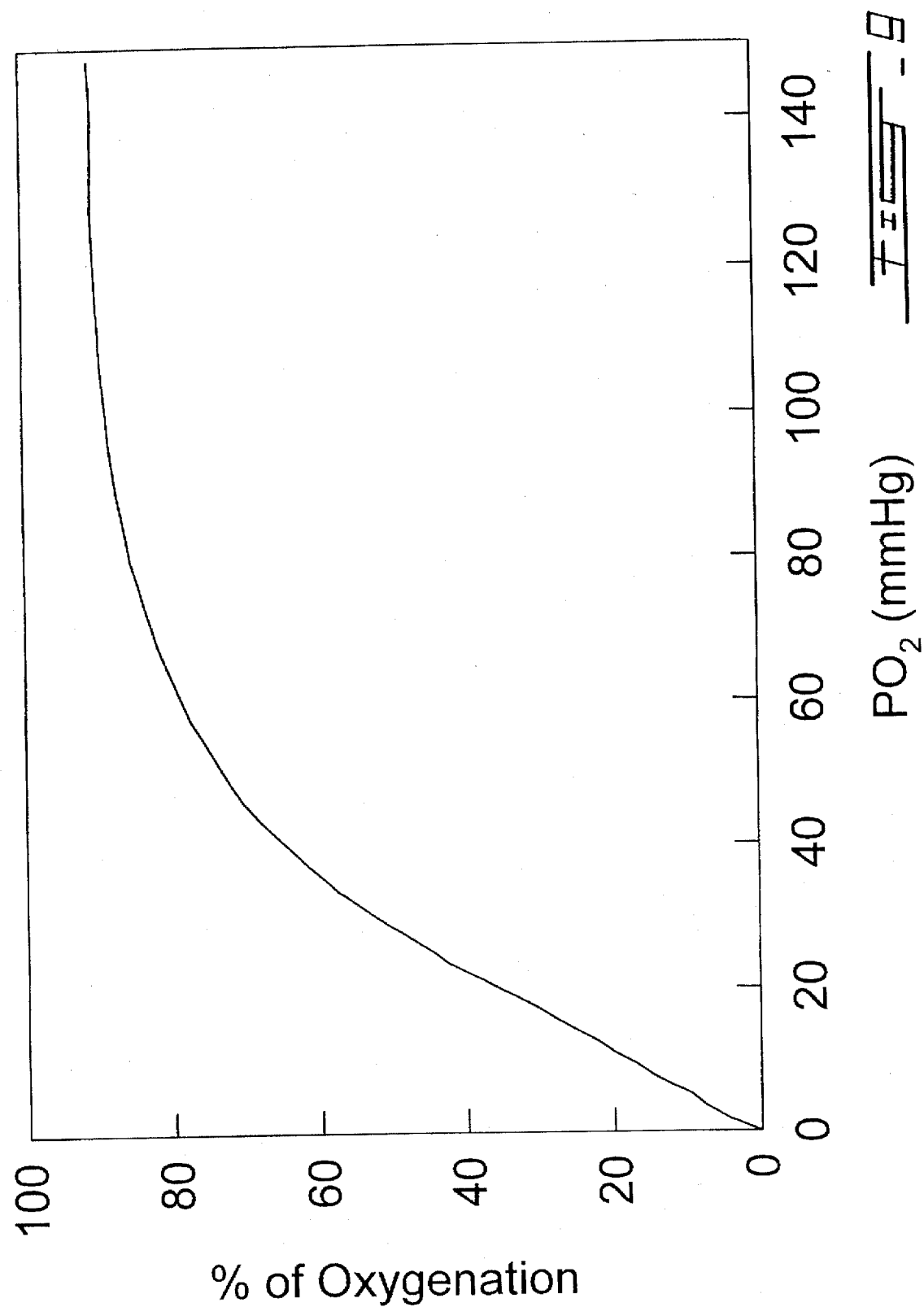
FIG. 9 is an oxygen dissociation curve of polymer membrane particles consisting of isobultyl-2-cyanoacrylate and containing 27% by weight of hemoglobin with a mean diameter of 0.389μ.
Figure 10:
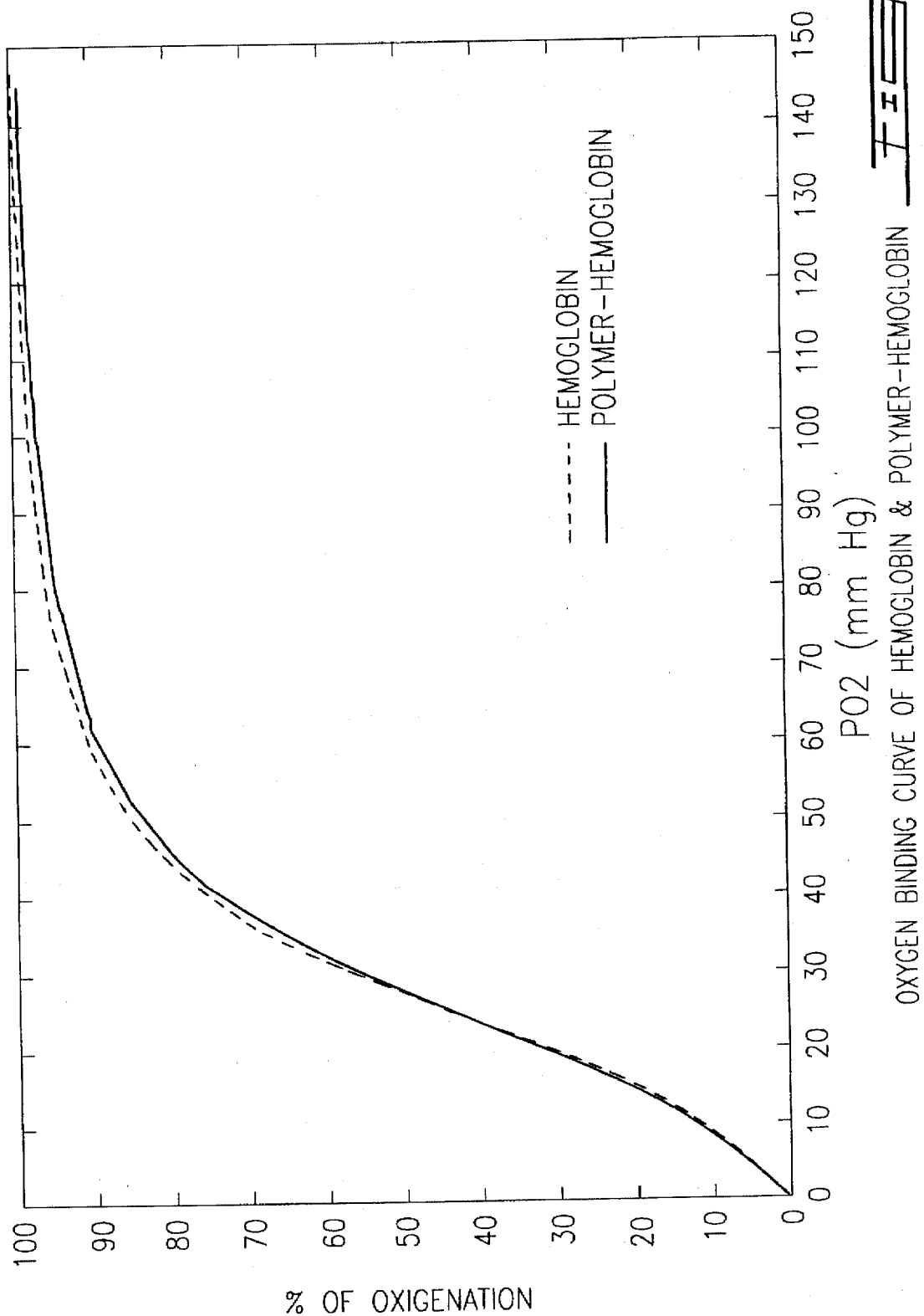
FIG. 10 is an oxygen dissociation curve of polymer membrane particles consisting of isobultyl-2-cyanoacrylate and containing 27% by weight of hemoglobin with a mean diameter of 0.389μ.

Oxygen dissociation curves of such a preparation is made by the TCS Hemoxanalyser™. A curve of one such polymer preparation is shown in FIGS. 6, 9 and 10. The P50 of the biodegradable polymer membrane particles containing bovine hemoglobin is 32 mmHg. The oxygen carrying and release properties are therefore as good as those of the red blood cells. A small change in the curve is noted in oxygen saturation at high oxygen pressure.

The oxygen dissociation curves of hemoglobin solution (FIG. 9) and poly-IBCA (FIG. 10) showed no difference, which demonstrate that the procedure of the Poly-IBCA do not damage the hemoglobin.

EXAMPLE IV

Determination of Oxygen Affinity of Biodegradable Polymer Membrane Containing Hemoglobin (IBCA)

Figure 11:
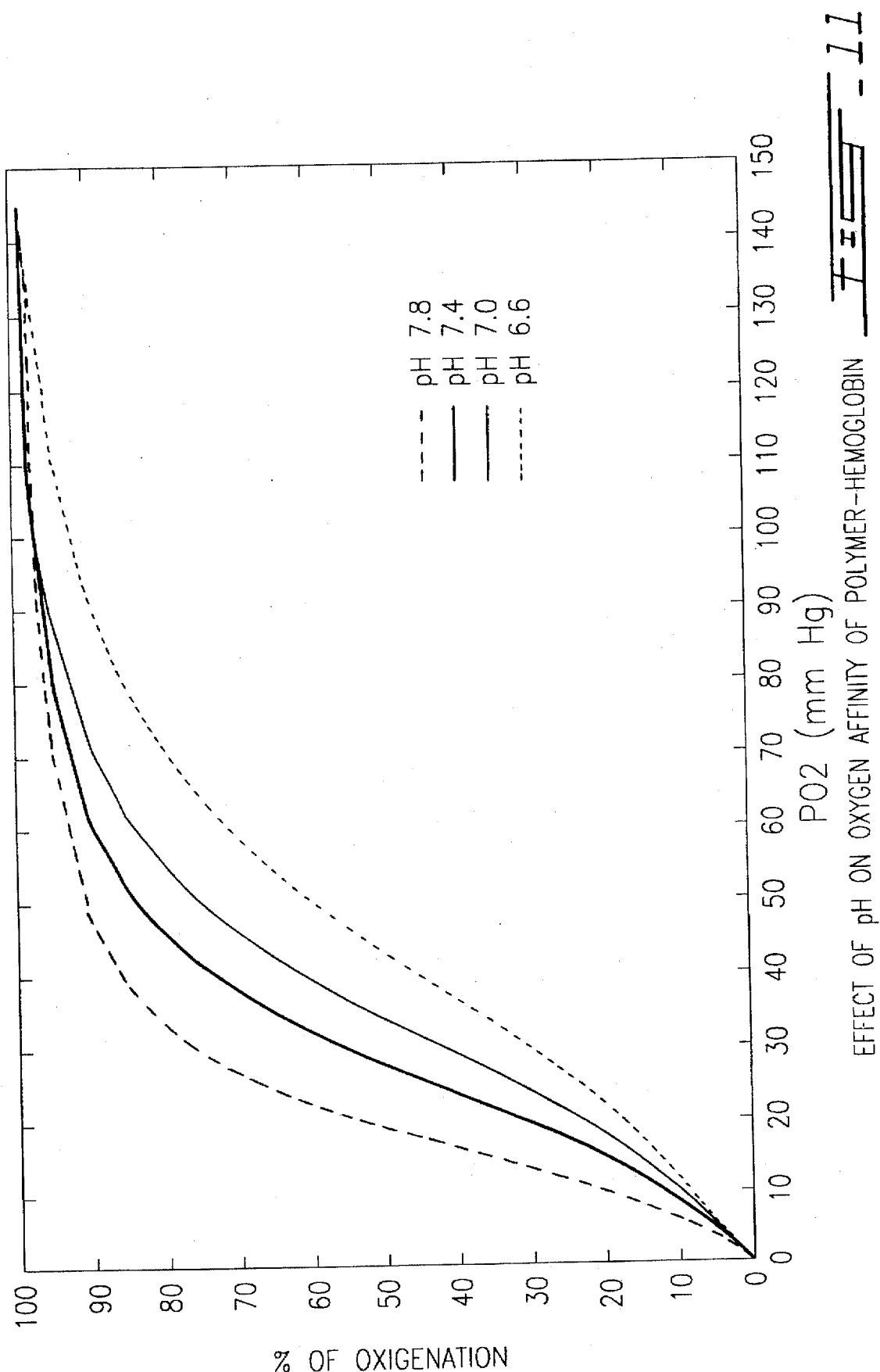
FIG. 11 is a curve of the effect of pH on oxygen affinity of polymer membrane particles consisting of polylactic acid and containing hemoglobin.
Figure 17:
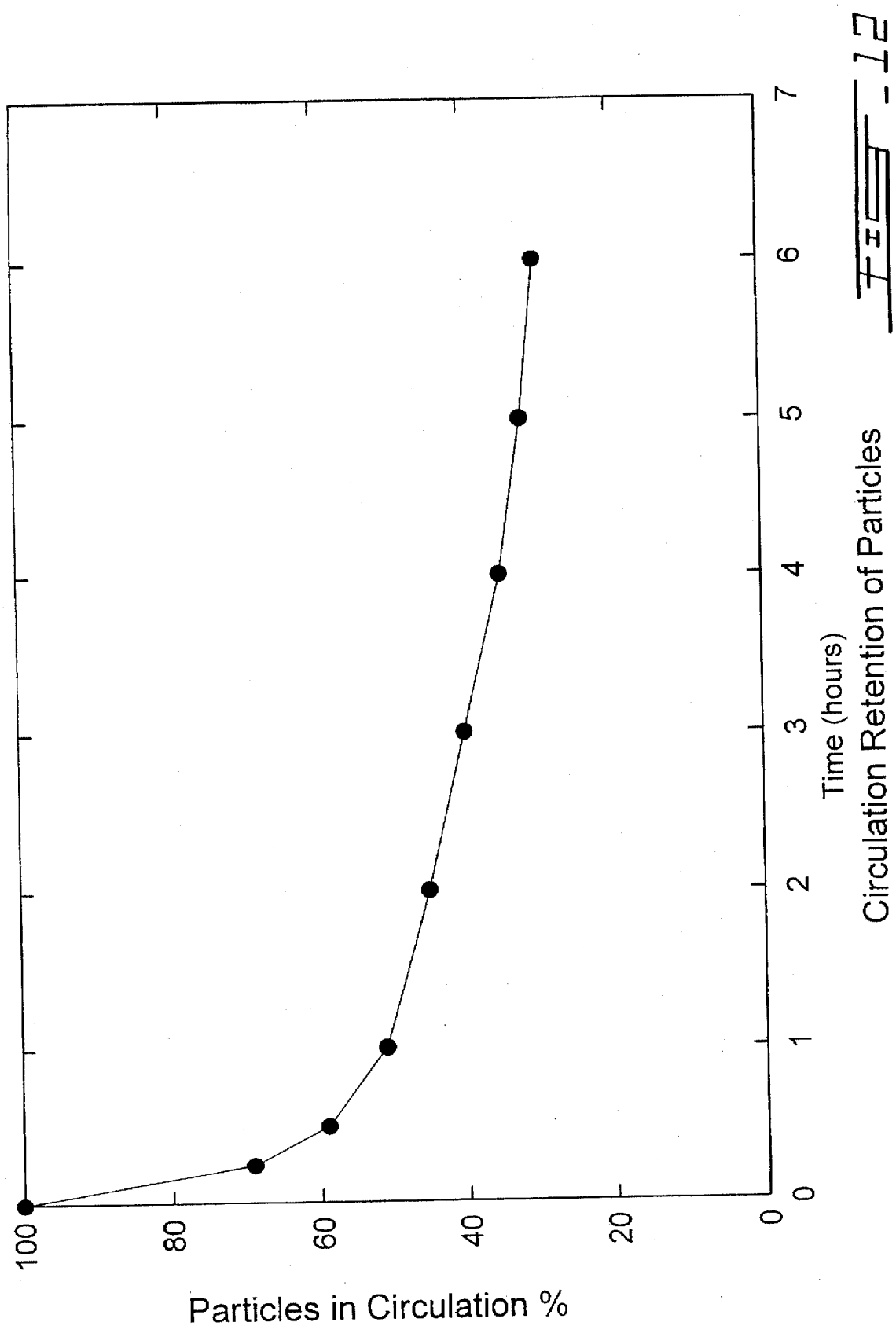

The oxygen dissociation curves of the hemoglobin solution and of the polymer membrane particles of Example I containing hemoglobin, are shown in FIG. 11. No difference between the two curves are found. The P50 of polymer particle preparation and the P50 of the hemoglobin are in good agreement. This means that the procedure used for the preparation of the polymer particles does not damage the encapsulated hemoglobin.

In the physiological pH range, the oxygen affinity of these polymer membrane particles containing hemoglobin varies depending on the pH as illustrated in FIG. 12. The bohr effect is about −0.22 to −0.24.

EXAMPLE V

In Vivo Test of Biodegradable Polymer Particles Containing Hemoglobin

The rat is injected with a volume of the particles suspension of Example I containing hemoglobin equivalent to 30% to 100% of their blood volume. Blood samples are withdrawn at intervals from the vein and centrifuged in microhematocrit tubes.

The survival time of the particles in blood is determined by measuring the turbidity in the plasma by using a micro centrifugal analyzer (Multistat III plus ™, Instrumentation Laboratory, Lexington, Mass.).

FIG. 13 illustrates the time required for disappearance of the biodegradable particles from the animal's circulation.

The preliminary in vivo test illustrates that the particles of the present invention can circulate in the body and their half-life is about six (6) hours.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A process for the production of a submicron diameter of less than 0.2µ biocompatible and biodegradable polymer membrane containing hemoglobin and enzymes comprising the steps of:
   a) mixing a polymer selected from the group consisting of isobutyl 2-cyanoacrylate and alkylcyanoacrylate derivatives with phospholipid and tocopherol;
   b) dissolving the mixed solution of step a) in ethanol;
   c) injecting the mixed solution of step b) in a hemoglobin solution containing surfactant to spontaneously form submicron diameter particles of polymer membrane containing hemoglobin;
   d) removing ethanol by dialysis;
   e) separating said submicron diameter particles of step c) by centrifugation or gel filtration; and
   f) suspending said particles of step e) in a saline ringer solution.

2. A process for the production of a submicron diameter of less than 0.2µ biocompatible and biodegradable polymer membrane containing hemoglobin and enzymes comprising the steps of:
   a) mixing a polymer selected from the group consisting of polylactic acid, polyglycolic acid and polylactide-co-glycolide with phospholipid and tocopherol;
   b) dissolving the mixed solution of step a) in a solution of ethanol and acetone;
   c) injecting the mixed solution of step b) in a hemoglobin solution containing surfactant to spontaneously form submicron diameter particles of polymer membrane containing hemoglobin;
   d) removing ethanol and acetone by dialysis;
   e) separating said submicron diameter particles of step c) by centrifugation or gel filtration; and
   f) suspending said particles of step e) in a saline ringer solution.

3. A submicron diameter biocompatible and biodegradable polymer membrane containing hemoglobin and enzymes used as an oxygen-carrying blood substitute, comprising a polymer selected from the group consisting of polylactic acid, polyglycolic acid and polylactide-co-glycolide containing from about 25 to 35% by weight of hemoglobin and having an average diameter of less than 0.2µ.

4. A submicron diameter biocompatible and biodegradable polymer membrane containing hemoglobin and enzymes used as an oxygen-carrying blood substitute, comprising a polymer selected from the group consisting of isobutyl 2-cyanoacrylate and alkylcyanoacrylate derivatives containing from about 25 to 35% by weight of hemoglobin and having an average diameter of less than 0.2µ.

5. The submicron diameter biocompatible and degradable polymer membrane according to claim 3, which further comprises a phospholipid.

6. The submicron diameter biocompatible and degradable polymer membrane according to claim 3, wherein said enzymes are selected from the group consisting of catalase, superoxide dismutase and methemoglobin reductase.

7. The submicron diameter biocompatible and degradable polymer membrane according to claim 4, wherein said enzymes are selected from the group consisting of catalase, superoxide dismutase and methemoglobin reductase.

* * * * *